United States Patent [19]

Bennett et al.

[11] Patent Number: 5,658,773
[45] Date of Patent: Aug. 19, 1997

[54] TOMATO ACID INVERTASE GENE

[75] Inventors: Alan B. Bennett; Ellen M. Klann, both of Davis, Calif.

[73] Assignee: The Regents of the University of California, Oakland, Calif.

[21] Appl. No.: 296,624

[22] Filed: Aug. 26, 1994

Related U.S. Application Data

[63] Continuation of Ser. No. 770,970, Oct. 7, 1991, abandoned.

[51] Int. Cl.$^6$ .............................. C12N 15/82; A01H 4/00
[52] U.S. Cl. ........................ 435/172.3; 435/6; 800/205; 800/DIG. 44
[58] Field of Search ................... 536/23.2; 435/320.1, 435/172.3, 6, 69.1; 800/205, DIG. 44; 530/370

[56] References Cited

U.S. PATENT DOCUMENTS 5,434,344  7/1995  Bennett et al. .................... 800/200

OTHER PUBLICATIONS

Walker, A.J. and Ho, L.C., "Carbon Translocation in the Tomato: Carbon Import and Fruit Growth," *Ann. Bot.* 41: 813–823 (1977).

Walker, A.J. and Thornley, J.H.M., "The Tomato Fruit: Import, Growth, Respiration and Carbon Metabolism at Different Fruit Sizes and Temperatures," *Ann. Bot.*, 41: 977–985 (1977).

Hewitt, J. D., et al., "Sink Strength of Fruits of Two Tomato Genotypes Differing in Total Fruit Solids Content," *J. Amer. Soc. Hort. Soc.,* 107(5): 896–900 (1982).

Hewitt and Garey, *Tomato Biotechnology* 45–54 (Nevins and Jones, eds. 1987).

Yelle et al., *Plant Physiol.* 87:737–740 (1988).

Rick, *Hilgardia*, 42:494–509 (1974).

Yelle et al., *Plant Physiol.* 95:1026–1035 (1991).

Sturm et al., *Plant Cell,* 2:1107–1119 (1990).

Davies, *Nature,* 209:640–641 (1966).

Yelle, et al Plant Physiol. 95:1026 (1991).

Helfman, et al (1987) in Methods in Enzymology 152:451–457.

Sturm, et al (Nov. 1990) The Plant Cell 2:1107–1119.

Wallace, et al (1987) Methods in Enzymology 152:432–442.

Fuqua, et al (1990) BioTechniques 9(2):206–210.

Smith, et al (1990) Plant Molecular Biology 14:369–379.

Yelle, et al Plant Physiology 87:737 (1988).

Dickinson, et al (1991) Plant Physiol. 95:420–425.

Boswell et al in *Computational Molecular Biology, Sources and Methods for Sequence Analysis* (Lisk, ed.) pp. 170–171, Oxford University Press, Oxford, 1988.

*Primary Examiner*—Che S. Chereskin
*Attorney, Agent, or Firm*—Townsend and Townsend and Crew LLP

[57] ABSTRACT

The present invention relates generally to methods for modifying the sucrose content of fruit. In particular, it relates to methods for increasing fruit sucrose content by inhibiting the expression of acid invertase. Additionally, it relates to methods for decreasing fruit sucrose content and increasing fruit hexose content by over expressing acid invortase.

9 Claims, No Drawings

TOMATO ACID INVERTASE GENE

This is a Continuation of application Ser. No. 07/770,970 filed Oct. 7, 1991 now abandoned.

BACKGROUND OF THE INVENTION

1. Field of the Invention

The present invention relates generally to methods for modifying the sucrose content of fruit. In particular, it relates to methods for increasing fruit sucrose content by inhibiting the expression of acid invertase. Additionally, it relates to methods for decreasing fruit sucrose content and increasing fruit hexose content by over expressing acid invertase.

A molecular genetic approach to altering sucrose accumulation in fruit is desirable because it is more precise and reproducible than using breeding plans. Breeding plans are laborious and require introduction of a trait found in wild type plants such as *L. chmielewskii* into non-wild plants such as *L. esculentum*. The desired trait may be linked to many undesired traits such as small, non-red, nonripening fruit and to a trait rendering the plant sterile. Also, the molecular genetic approach is applicable to many species for which gene transfer technology is available. Finally, cloning a gene permits elaboration of its end product in quantity.

2. Information Disclosure

Generally, a high soluble solids content is desirable in tomatoes because of its economic significance. Hewitt and Garrey, *Tomato Biotechnology*, 45–54 (Nevins and Jones, eds. 1987). Increased accumulation of sucrose contributes to elevation of the soluble solids content. U.S. patent application Ser. No. 509,673. The fruit of the commercially grown tomato cultivar, *Lycopersicon esculentum*, accumulate glucose and fructose, but not sucrose. Yelle et. al., *Plant Physiol*, 87:737–740 (1988). Breeding plans have produced at least one variety showing increased soluble solids. Rick, *Hilgardia*, 42:494–509 (1974). Work with one breeding plan resulted in the introduction of a genetic factor that confers on tomato plants the ability to bear mature fruit which accumulate sucrose, thereby increasing the total soluble solids content of the fruit. Patent application Ser. No. 509,673.

Generally, sucrose may be broken into the hexose sugars glucose and fructose by the enzyme invertase. Genetic and biochemical attributes of invertase have been studied. Yelle et. al., *Plant Physiol*. 95:1026–1035 (1991). Carrot acid invertase has been cloned. Sturm et. al., *Plant Cell*, 2:1107–1119 (1990). There are two regions of close similarity between genes encoding invertase and sucrose hydrolase. Sturm at 1115. The fruit of *Lycopersicon chmielewskii*, *L. hirsutum*. and *L. peruviatum* have been shown to accumulate sucrose instead of glucose and fructose. Davies, *Nature*, 209:640–641 (1966). The prior art does not teach the expression of tomato acid invertase in elevated levels in cell lines or manipulation of its activity using recombinant techniques.

SUMMARY OF THE INVENTION

The present invention provides a method for increasing sucrose content by inhibiting the activity of acid invertase in various agronomically important species. In the exemplified case, cDNA from the tomato acid invertase gene is used to create expression cassettes comprising antisense DNA or RNA in the native orientation to control the activity of the gene. Additionally, the invention provides a method to decrease the sucrose content by over-expressing the activity of the gene by using DNA constructions encoding acid invertase.

Recombinant DNA techniques are used to introduce the antisense cDNA sequence into a suitable vector which is subsequently used to transform a suitable host cell. In the exemplified case, *Agrobacterium tumefaciens* is used as a vehicle for transmission of the cDNA to the ultimate host, the tomato cell. A plant regenerated from the transformed cell transcribes the antisense cDNA which inhibits synthesis of the enzyme. In plant cells, it has been shown that antisense cDNA inhibits gene expression by preventing the accumulation of mRNA which results in decreased levels of the protein encoded by the gene.

This invention could be practiced by inserting into plants expression cassettes affecting expression of an endogenous acid invertase gene. Antisense genes under the control of appropriate regulatory elements could decrease expression of the endogenous gene and confer the trait of sucrose accumulation. Alternatively, certain situations may warrant the conversion of stored sucrose to hexoses. This conversion could be accomplished by over expressing the acid invertase gene in the appropriate developmental context.

DETAILED DESCRIPTION

The present invention relates to methods of modifying sucrose content of fruit by altering the expression of acid invertase. The invention provides a method for increasing the sucrose content of fruit comprising introducing into a plant an expression cassette having a plant promoter sequence operably linked to a DNA subsequence of at least 20 base pairs derived from a DNA sequence encoding acid invertase, the DNA subsequence being linked to the promoter sequence in the opposite orientation for expression. The promoter can be either constitutive or inducible. If constitutive, it is preferably the 35S promoter of cauliflower mosaic virus. If inducible, it is preferably derived from the tomato E8 gene.

Additionally, the invention provides a method for decreasing sucrose content of fruit comprising introducing into a plant an expression cassette having a plant promoter sequence operably linked to a DNA subsequence of at least 20 base pairs derived from a DNA sequence encoding acid invertase, the DNA subsequence being linked to the promoter sequence in the correct orientation for expression. Again, the promoter can be either constitutive or inducible. If constitutive, it is preferably the 35S promoter of cauliflower mosaic virus. If inducible, it is preferably derived from the tomato E8 gene.

The preferred plant for the method is tomato. The expression cassette can be introduced into the plant by any in vitro technique, preferably using Agrobacterium. The expression cassette can also be introduced into the plant by a sexual cross.

The present invention also provides a method of inhibiting invertase activity comprising, introducing into a plant an expression cassette having a plant promoter sequence operably linked to a DNA subsequence of at least 20 base pairs derived from a DNA sequence encoding acid invertase, the DNA subsequence being linked to the promoter sequence in the opposite orientation for expression. By inhibiting the synthesis of the enzyme, the conversion of sucrose to the hexose sugars can be diminished. The preferred embodiments as described above apply to this method as well.

The present invention further provides an expression cassette comprising a plant promoter sequence operably linked to a DNA subsequence of at least 20 base pairs derived from a DNA sequence encoding acid invertase, the DNA subsequence being linked to the promoter sequence in the opposite orientation for expression. The promoter can be constitutive, typically derived from cauliflower mosaic virus, or inducible, typically the E8 promoter.

A plant, preferably tomato, is also provided that contains an expression cassette having a plant promoter sequence operably linked to a DNA subsequence of at least 20 base pairs derived from a DNA sequence acid invertase. The DNA subsequence may be linked to the promoter sequence in the opposite orientation for expression to decrease the synthesis of invertase, or linked in the correct or native orientation to increase the expression of invertase.

The present invention further provides a DNA sequence which is uninterrupted, which encodes acid invertase, and which is flanked on at least one side by non-wild type DNA. The DNA sequence is typically a cDNA sequence derived from tomato.

Further, an expression cassette is provided which comprises a promoter sequence operably linked to a DNA sequence which is uninterrupted and which encodes acid invertase. The DNA sequence is typically a cDNA sequence derived from tomato. The promoter sequences function in both prokaryotes and eukaryotes.

The present invention also provides a method of isolating from a plant a DNA sequence encoding acid invertase comprising, probing a DNA library prepared from plant tissue with oligonucleotide probes comprising a sequence from the acid invertase cDNA. The DNA library can be either a genomic or cDNA library. A genomic structure relating to the present invention may be about 10,000 basepair long. This includes the gene encoding tomato acid invertase of about 3k bp, promoter of about 3k bp, terminator sequence of about 400 bp, regulatory sequence and the genetic environment. A tomato genomic library has been prepared and is available. To probe a DNA library, the preferred sequences are:

```
5' ATG GAA TAT ACI GGI GAT 3'
        G   C           C
``` designated Seq. I.D. No. 3 and

```
3' CTA ATA CAI GTT CAI CTT TTA AAI CGI ATA 5'
    G   G   C       C   G G           G
``` designated Seq. I.D. No. 4.

A DNA construct is provided comprising a promoter sequence operably linked to a DNA sequence encoding a signal peptide from tomato acid invertase, the DNA sequence being joined to other than a sequence encoding mature tomato acid invertase. Finally, the cDNA sequence provided by this invention can be used to construct vectors capable of expressing fusion proteins comprised of an acid invertase signal peptide fused to any foreign gene. This provides for the secretion of foreign gene products from the plant cell.

In summary, cloned cDNA encoding acid invertase was prepared by 1) purifying the protein (invertase) from the hexose accumulating tomato fruit of *L. esculentum*, 2) determining portions of the protein amino acid sequence, 3) constructing oligonucleotide probes corresponding to the amino acid sequence, 4) screening a tomato fruit cDNA library, 5) verifying the identity of the cDNA by nucleotide sequencing, and 6) suggesting the role of the gene in conferring the trait of sucrose accumulation by mapping its chromosomal location.

Briefly, the manipulations to prepare antisense invertase cDNA and introduce it into a plant cell involved 1) isolating mRNA from ripe fruit, 2) preparing cDNA from the mRNA, 3) screening the cDNA for the desired sequence, 4) linking a plant promoter to the desired cDNA in the opposite orientation for expression of the invertase gene, 5) transforming suitable host plant cells, and 6) selecting and regenerating cells which contain the inverted sequence. Also, cDNA constructions in the sense or native orientation can be prepared in like fashion, but at step 4) the prompter and cDNA are linked in the orientation for expression of the gene.

The following descriptions will detail various methods available to introduce and express foreign DNA sequences in plant cells. Specific examples of preferred methods are also described.

I. General Methods

Generally, the nomenclature used hereafter and the laboratory procedures in recombinant DNA technology described below are those well known and commonly employed in the art. Standard techniques are used for cloning, DNA and RNA isolation, amplifications and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989. The manual is hereinafter referred to as "Sambrook". Other general references are provided throughout this document. The procedures therein are believed to be well known in the art and are provided for the convenience of the reader. All the information contained therein is incorporated herein by reference.

Tomato acid invertase was cloned by obtaining internal protein sequences from purified acid invertase cleaved with cyanogen bromide, making DNA oligonucleotides to match the coding sequence predicted for the known protein sequence, and using the resulting oligonucleotides to probe a plasmid cDNA library. To obtain the 5' end of the cDNA, the method used was rapid amplification of cDNa ends polymerase chain reaction. Frohman, *Amplifications: a Forum for PCR Users* (September 1990).

II. Preparation of Acid Invertase cDNA

The nucleotide sequence of the cDNA encoding tomato acid invertase is provided in sequence I.D. number 1. The cDNA was deposited with the American Type Culture Collection, Rockville, Md. on Oct. 4, 1991 and has Accession No. 75118. This deposit is available. A Sal I digestion of DNA and a Sal I digestion of Bluescript is performed as described below to utilize the deposit.

To prepare acid invertase cDNA, mRNA from ripe fruit is first isolated. Eukaryotic mRNA has at its 3' end a string of adenine nucleotide residues known as the poly-A tail.

Short chains of oligo d-T nucleotides are then hybridized with the poly-A tails and serve as a primer for the enzyme reverse transcriptase. This enzyme uses RNA as a template to synthesize a complementary DNA strand. A second DNA strand is then synthesized using the first cDNA strand as a template. Linkers are added to the double-stranded cDNA for insertion into a plasmid or λ phage vector for propagation in *E. coli*.

Identification of clones harboring the desired cDNA is performed by either nucleic acid hybridization or immunological detection of the encoded protein, if an expression vector is used. The bacterial colonies are then replica plated on nitrocellulose filters. The cells are lysed and probed with either oligonucleotides complementary to the desired cDNA or with antibodies to the desired protein. The nucleotide sequence of the cDNA encoding tomato acid invertase may be used in any of a number of ways. It may be used to express acid invertase or fragments of the sequence may be used as probes to identify acid invertase genes in genomic or cDNA libraries prepared from other plant species.

The cDNA can be inserted in the antisense direction into expression cassettes to inhibit the expression of the acid invertase gene in plant cells. The cDNA sequence in the native or sense direction can also be inserted in an expression cassette for expression in bacteria or plant cells.

The sequence provided can also be used for expression of fusion proteins comprised of a portion of an acid invertase enzyme fused to another protein. Of particular interest is the transit peptide sequence of the protein. As is well known in the art, proteins transported across the cell membrane typically have an N-terminal sequence rich in hydrophobic amino acids about 15 to 30 amino acids long. Sometime during the process of passing through the membrane, the signal sequence is cleaved by signal peptidase. Watson et al., *Molecular Biology of the Gene*, p. 731, 1987. Thus, the signal peptide encoding sequence of a tomato acid invertase gene may be linked to another, foreign, structural gene to provide for transport of the foreign gene product to the cell wall or vacuole. The foreign structural gene may be derived from any source including bacteria, yeast, animals or plants. Typically, the signal peptide encoding sequence will be joined at its 3' end to a linker for attachment to the foreign structural gene in the proper reading frame. Foreign genes of interest include those responsible for synthesis of carbohydrate and cell wall metabolizing enzymes. Examples include include genes controlling production of cellulose, polygalacturonase, enzymes contained in a vacuole, and targeting genes to vacuoles.

III. Vector Construction

The desired recombinant vector will comprise an expression cassette designed for initiating transcription of the antisense cDNA in plants. Companion sequences, of bacterial or viral origin, are also included to allow the vector to be cloned in a bacterial or phage host.

The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

A bacterial expression vector may be used if expression of an acid invertase cDNA in bacteria is desired. Construction of a bacterial expression vector is typically done by placing the cDNA downstream from a strong bacterial promoter. Examples of bacterial promoters that might be used include β-lactamase, β-galactosidase, and the phage λpL promoters. The efficiency of translation of mRNA in bacteria is critically dependent on the presence of a ribosome-binding site and its distance from the transcription initiation codon.

For expression in plants, the recombinant expression cassette will contain in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Other sequences conferring tissue specificity, response to environmental signals, or maximum efficiency of transcription my also be found in the promoter region. Such sequences are often found within 400 bp of transcription initiation size, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. Herrara-Estrella et al., *Nature*, 303:209–213, 1983. Viral promoters include the 35S and 19S RNA promoters of cauliflower mosaic virus. Odell et al. *Nature*, 313:810–812, 1985. The 35S RNA promoter was used in the present invention. Possible plant promoters include the ribulose-1,3-bisphosphate carboxylase small subunit promoter and the phaseolin promoter. The promoter sequence from the E8 gene and other genes may also be used. The promoter sequence from the E8 gene was used in the present invention. The isolation and sequence of the E8 promoter is described in detail in Deikman and Fischer, *EMBO J.* 7:3315–3327, 1988. which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434, 1982. Polyadenylation is of importance for expression of acid invertase cDNA in plant cells. Polyadenylation sequences include, but are not limited to the Agrobacterium octopine synthase signal (Gielen et al., *EMBO J.*, 3:835–846, 1984) or the nopaline synthase signal (Depicker et al., *Mol. and Appl. Genet*, 1:561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow an a medium containing the particular antibiotic.

IV. Transcription of Acid Invertase Antisense cDNA in Plant Cells

A. Transformation of Plant Cells by in vitro Techniques

1. Direct Transformation

The vector described above can be microinjected directly into plant cells by use of micropipettes to mechanically transfer the recombinant DNA. Crossway, *Mol. Gen. Genetics*, 202:179-185, 1985. The genetic material may also be transferred into the plant cell using polyethylene glycol, Krens, et al., *Nature*, 296, 72-74, 1982.

Another method of introduction of nucleic acid segments is high velocity ballistic penetration by small particles with the nucleic acid either within the matrix of small beads or particles, or on the surface, Klein, et al., *Nature*, 327, 70-73, 1987.

Yet another method of introduction is fusion of protoplasts with other entities, either minicells, cells, lysosomes or other fusible lipid-surfaced bodies, Fraley, et al., *Proc. Natl. Acad. Sci. USA*, 79, 1859-1863, 1982.

The DNA may also be introduced into the plant cells by electroporation. Fromm et al., *Pro. Natl Acad. Sci. USA*, 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

2. Vectored Transformation

Cauliflower mosaic virus (CaMV) may be used as a vector for introducing the antisense DNA into plant cells. (Hohn et al., 1982 *"Molecular Biology of Plant Tumors,"* Academic Press, New York, pp. 549-560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

Another method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. This method was used in the present invention.

Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237: 1176-1183, 1987.

Ti and Ri plasmids contain two regions essential for the production of transformed cells. One of these, named transferred DNA (T-DNA), is transferred to plant nuclei induces tumor or root formation. The other, termed the virulence (vir) region, is essential for the transfer of the T-DNA but is not itself transferred. The T-DNA will be transferred into a plant cell even if the vir region is on a different plasmid. Hoekema, et al., *Nature*, 303:179-189, 1983. The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These my include but are not limited to "shuttle vectors", (Ruvkun and Ausubel, 1981, Nature 298:85-88), promoters, (Lawton et al., 1987, Plant Mol. Biol. 9:315-324) and structural genes for antibiotic resistance as a selection factor (Fraley et al., *Proc. Nat. Acad. Sci.*, 80:4803-4807, 1983).

In conjunction with the present invention, two antisense constructs were made. In the first, bases 1-1653 of the full length cDNA were ligated in the antisense orientation after the CaMV 35S promoter in place of the GUS gene in the vector pBI121. In the second construct, bases 1-1653 were ligated between the E8 promoter region and the nos terminator region in the antisense orientation. This cassette was then ligated into the vector pBIN19. Both plasmids were put into the Agrobacterium strain LBA 4404, and introduced into tomato cells.

All plant cells which can be transformed by Agrobacterium and from which whole plants can be regenerated can be transformed according to the present invention to produce transformed intact plants which contain the desired DNA. There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for culturing protoplasts and subsequent plant regeneration from cultured protoplasts.

Method (2) requires (a) that the intact plant tissues, such as cotyledons, can be transformed by Agrobacterium and (b) that the transformed cells or tissues can be induced to regenerate into whole plants. Method (2) was used in the present invention.

Most dicot species can be transformed by Agrobacterium. All species which are a natural plant host for Agrobacterium transformable in vitro. Monocotyledonous plants, and in particular, cereals, are not natural hosts to Agrobacterium. Attempts to transform them using Agrobacterium have been unsuccessful until recently. Hooykas-Van Slogteren et al., *Nature,* 311:763–764, 1984. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed.

B. Selection and Regeneration of Transformed Plant Cells

After transformation, transformed plant cells or plants comprising the antisense DNA must be identified. A selectable marker, such as those discussed, supra, is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well. See, e.g., Sambrook, supra.

After determination of the presence of the antisense DNA, whole plant regeneration is desired. All plants from which protoplasts can be isolated and cultured to give whole regenerated plants can be transformed by the present invention. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, and Datura.

Plant regeneration from cultured protoplasts is described in Evans et al., *Handbook of Plant Cell Cultures,* Vol. 1: (MacMillan Publishing Co. New York, 1983); and Vasil I. R. (ed.), *Cell Culture and Somatic Cell Genetics of Plants,* Acad. Press, Orlando, Vol. I, 1984, and Vol. III, 1986.

It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induces in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

V. Purification of Protein

The present invention provides an enzyme, acid invertase. Enzyme purification is known in the art. The acid invertase of the present invention can be purified according to standard procedures of the art, including ammonium sulfate precipitation, affinity and fraction column chromatography, gel electrophoresis and the like, (See, generally, Scopes, R., *Protein Purification,* Springer-Verlag, N. Y. (1982), and U.S. Pat. No. 4,512,922 disclosing general methods for purifying protein from recombinantly engineered bacteria.

To purify invertase from tomato fruit, the method of Yelle can be used. Yelle, *Plant Physiol.,* 95:1026–1035 (1991), incorporated herein by reference. Yelle's method is followed through the step using the Mono Q column. Those fractions are dialyzed against water at 4° C., precipitated with 0.1 volumes of a 100% trichloroacetic acid\0.4% deoxycholate solution, washed with acetone and dried. The protein is resuspended in Laemmli SDS-PAGE sample buffer, boiled ten minutes, and applied to a standard 15% Laemmli system preparative gel which has been poured the night before. The gel is stained with 10% methanol, 0.5% acetic acid, and 0.1% coomassis blue R250 for twenty minutes. After destaining the gel for about 1.5 hours in 10% methanol, the prominent protein band at 50 kD is excised. The protein is eluted from the gel slice in a 12–14 kD cutoff dialysis bag in 0.5× PAGE tank buffer. The elutant is dialyzed against water at 15° C.

Acid invertase may also be expressed and purified from eukaryotic cells and prokaryotes other than tomato. If the expressed protein is excreted, a number of the steps used in purification from tomato fruit can be applied. Following the growth of the recombinant cells and concomitant secretion of invertase into the culture media, this "conditioned media" is harvested. The conditioned media is then clarified by centrifugation or filtration to remove cells and cell debris. The proteins contained in the clarified media are concentrated by adsorption to any suitable resin such as, for example, an anion exchange resin, or by use of ammonium sulfate fractionation, polyethylene glycol precipitation, or by ultrafiltration. Other routine means known in the art may be equally suitable. Further, the purification of invertase secreted by cultured cells may require the additional use of, for example, affinity chromatography, ion exchange chromatography, sizing chromatography or other protein purification techniques to obtain homogeneity.

In some cases, the expressed protein may not be excreted. If the cell line has a cell wall, then initial extraction in a low salt buffer may allow the acid invertase to pellet with the cell wall fraction as is the case with tomato fruit. Then all the protein may be eluted from the cell wall with high salt and then dialyzed. If the cell line allows the protein to be glycosolated in a manner similar to the tomato cell. The purified glycoprotein may also be enhanced by using a Con A column. Anion exchange columns (MonoQ, Pharmacia) and gel filtration columns may be used to further purify the acid invertase. If a highly pure preparation is desired, this may be achieved at the expense of enzyme activity by denaturing preparative polyacrilamide gel electrophoresis.

VI. Definitions

The term "antisense" refers to the opposite orientation for expression.

The term "biologically pure" refers to a recombinantly produced product substantially free of proteins of tomato origin other than the product itself.

A "constitutive" promoter is a promoter which is active under all environmental conditions and all states of development or cell differentiation.

An "inducible" promoter is a promoter which is under environmental or developmental control.

The term "invertase" means an enzyme occurring in yeasts and other organisms including prokaryotes and eukaryotes that catalyzes the conversion of sucrose to hexoses. It is also referred to as β-fructofuranosidase.

The term "expression" refers to the transcription and translation of a structural gene so that a protein is synthesized.

A "heterologous sequence" or "heterologous expression cassette" is one that originates from a foreign species, or, if from the same species, is substantially modified from its original form.

The term "homology" means "identity" so that homologous nucleic acids possess basepair identity and order; homologous proteins or peptides possess amino acid identity and order.

The term "non-wild type DNA" refers to DNA sequences that do not flank a given DNA sequence in its naturally occurring environment.

The phrases "nucleic acid sequence" or "nucleic acid segment" refer to a single or double-stranded polymer of deoxyribonucleotide or ribonucleotide bases read from the 5' to the 3' end. It includes both self-replicating plasmids, infectious polymers of DNA or RNA and non-functional DNA or RNA.

The term "operably linked" refers to functional linkage between a promoter and a second sequence, wherein the promoter sequence initiates transcription of RNA corresponding to the second sequence.

The term "opposite orientation for expression" refers to a double-stranded DNA sequence from a structural gene that is inserted in an expression cassette in an inverted manner with respect to its naturally occurring orientation. Specifically, the strand that is normally the "template strand" becomes the coding strand, and vice versa.

The term "plant" includes whole plants, plant organs (e.g., leaves, stems, roots, etc.), seeds and plant cells.

The term "promoter" refers to a region of DNA upstream from the structural gene and involved in recognition and binding RNA polymerase and other proteins to initiate transcription. A "plant promoter" is a promoter capable of initiating transcription in plant cells.

The phrase "suitable host" refers to a microorganism or cell that is compatible with a recombinant plasmid, DNA sequence or recombinant expression cassette and will permit the plasmid to replicate, to be incorporated into its genome, or to be expressed.

The term "uninterrupted" refers to a DNA sequence (e.g., cDNA) containing an open reading frame that lacks intervening, untranslated sequences.

The following experimental results are offered by way of example and not by way of limitation.

EXAMPLES

C. Preparation of Tomato Acid Invertase cDNA 1. cDNA Library Production

A vector-primed cDNA library was prepared using standard methods. The library was prepared in the cloning vector pARC7 from ripe tomato fruit poly-A-RNA by the method of Alexander et al., Gene, 31:79–89, 1984, which is incorporated herein by reference.

2. cDNA Library Screening a. Growing Colonies

HB101 cells containing a red ripe tomato-derived cDNA library were titered and dilutions were made to give approximately 5000 colonies per 10 ml of Luria Broth (LB). Ten ml aliquots of chilled bacterial suspension were vacuum filtered onto ten 132 mm nitrocellulose filters, which were then placed colony sides up on LB-agar plates containing 100 ug/ml ampicillin. Plates were incubated at 37° C. until colonies were approximately 0.5 mm in diameter.

b. Replica Plating

Master filters were removed from plates, numbered and given orientation marks with black ink. A fresh filter was wetted on a fresh LB plate and was laid on top of each master filter and orientation marks copied to the replicate. This process of colony transfer was repeated with a 2nd fresh filter to give two replica filters per master filter. Replicates were grown on LB-agar plates at 37° C. until colonies were approximately 0.5 mm and then were transferred to plates containing LB-agar with 150 ug/ml chloramphenicol. These were grown 12 hours at 37° C.

c. Bacterial Colony Lysis

Replica filters were removed from plates and placed colony sides up at room temperature on sheets of Whatman 3MM paper wetted with 0.5M NaOH/1.5M NaCl. After 10 minutes, filters were blotted on dry 3 MM paper and transferred for 2 minutes to 3 MM paper wetted with 1M Tris pH 7/1.5M NaCl. Filters were immersed in 3× SSC for 15 seconds, placed on dry 3 MM paper and air dried prior to baking at 80° C. under vacuum for 2 hours.

d. Hybridization to Oligonucleotide Probe

Bacterial debris was removed from baked filters by washing with 3× SSC/0.1% SDS at 62° C. for 24 hours, during which time wash solution was replaced with fresh solution 3 times. Filters were collectively prehybridized at 37° C. overnight with 6× SSC, 1× Denhardts Solution, 0.5% SDS, 0.05% NaPPi and 0.1 mg/ml boiled and ice-quenched salmon sperm DNA. The 20 filters were then divided into two groups of replicates for hybridization.

Oligonucleotide probes were synthesized at a DNA synthesizing facility. Probe sequences corresponded to sequenced portions of acid invertase protein. The preferred oligonucleotide probes are Seq. I.D. No. 3 and Seq. I.D. No. 4. Oligonucleotides were solubilized in 10 mM Tris-EDTA (TE) pH 8.0. DNA was resuspended and was brought to 2 mg/ml in TE pH 8.0.

One ug of each oligonucleotide probe was end labeled with 32P-ATP according to the T4 DNA Polymerase Labeling System (Bethesda Research Labs) protocol supplied by the manufacturer. Specific activity of each probe exceeded $2.4 \times 10^8$ cpm/ug.

After lysing the bacterial colonies on the filters, the filters were pre-hybridized for two hours at 37° C. The filters were hybridized with the labelled oligonucleotide in a hybridization bag overnight in an incubation chamber at 42° C. The hybridization bag contained a suitable amount of hybridization buffer and one of the boiled and ice-quenched radiolabeled probes. The hybridization medium was 6× SSC, 1× Denhardt's solution, 0.05% NaPPi and 0.1 mg/ml boiled and ice-quenched salmon sperm DNA.

Filters were washed at 47° C. in 6× SSC, 0.05% NaPPi for ten minutes. They were then exposed to Kodak X-O-Mat AR film at −80° C. for 24 hours using an intensifying screen. Film was developed and clones suspected of containing invertase probe sequence were identified via the comparison of orientation marks on the film with those on the corresponding master plate.

e. Secondary Screening of Putative Acid Invertase Clones

Colonies identified by acid invertase oligonucleotide probes were picked with sterile toothpicks and streaked on nitrocellulose filters. These filters were processed with replica plating, colony lysis and hybridization with labelled probes as described in steps b, c and d above. Single colonies of in the secondary screen were picked into 3 ml of LB with ampicillin 100 ug/ml and grown overnight at 37° C.

f. Southern Analysis of Acid Invertase Clones

Mini prep DNA was isolated from bacterial cultures by a method equivalent to Kraft et al. *Biotechniques* 6(6):544–546 which is incorporated herein by reference. DNA was then digested with Sal I restriction enzyme for an appropriate number of hours under standard conditions to release the cloned cDNA inserts from their respective pArc vectors; digestion products were size fractionated on 1.2% agarose gels. Following incubation with 0.5M NaOH/1.5M NaCl and finally by 0.5M Tris pH7/3M NaCl, gels were blotted to GeneScreen and probed with each oligonucleotide probe end labeled as previously described. The acid invertase insert was estimated to be 1.95 kilobases. This clone was selected for sequencing.

3. Sequencing of Tomato Acid Invertase a. Subcloning of Tomato Acid Invertase

Sal I digestion of DNA prepared from the colony described in step f described above released the 1.95 kB (estimated size) acid invertase clone from the pArc vector. Digestion products were precipitated with 0.4 volumes ammonium acetate and 2 volumes ethanol and resuspended in 1× DNA sample buffer. Products were loaded onto a standard 1.2% agarose gel with insert separated from vector by electrophoresis. The insert was run onto DEAE membranes and isolated using standard techniques. Sambrook. The DNA concentration was estimated using standard methods by comparing ethidium stained bands to the standards on agarose gel.

Bluescript vector (SK+) (Stratagene Inc., La Jolla, Calif.) was linearized by Sal I digestion under standard conditions at 37° C. After a suitable period of hours, digested vector was extracted once with phenol:chloroform:isoamyl alcohol (25:24:1) and once with chloroform-isoamyl alcohol (24:1) prior to precipitation with 0.4 volumes ammonium acetate and 2.5 volumes ethanol. The pelleted DNA was brought up in 50 mM Tris, 0.1 mM EDTA, pH 8.

The vector was ligated at 15° C. for 12 hours to melted invertase insert from the 1.2% agarose gel. Ligation specifications were as follows for each 45 ul ligation: total DNA concentration=200 ng/10.5 ul, insert:vector= 1:1 on a molar basis. T4 DNA ligase=100 units/ml, final PEG concentration=5%.

Ligation mixtures were brought up to 100 ul with TE 8.0 and added to 200 ul freshly thawed competent XL1 Blue *E. coli* cells. After 30 minutes on ice, cells were heat shocked 5 minutes at 37° C. Cells were shaken at 250 rpm on an orbital shaker for about two hours at 37° C. and transferred to ice. Appropriate aliquots of about 100 ul of the cells were then spread on LB agar plates containing appropriate antibiotics such as 100 ug/ml ampicillin and 50 ug/ml tetracycline. Plates had been pre-spread with 100 ul of (50 ul 100 mM IPTG, 20 ul 20 mg/ml X-gal, 30 ul LB). Plates were then incubated overnight at 37° C., at which time transformed colonies (white) could be distinguished from non-transformed colonies (blue). DNA was isolated from transformants as previously described and digested with Sal I to release inserts. One invertase transformant of approximately 1.95 kB was identified following the electrophoretic separation of digestion products on a 1.2% agarose gel. Double stranded miniprep DNA was prepared as described in *BioTechniques*, 9:676–679 (1990) for sequencing purposes.

b. Sequencing

Double stranded DNA template was created with restriction enzyme digestion and gene specific primers were used. Sequencing was conducted by the dideoxy method (Sanger, et al., *Proc Nat Acad Sci USA* 74:5463–5467) outlined fully in the Sequenase kit (United States Biochemical Co.) protocol provided by the manufacturer. Reverse M13 primer was purchased from Pharmacia.

Sequence data generated was entered and analyzed using the Microgenie sequence analysis computer program (Beckman Instruments, Inc.) strand resulted from the overlap of over 20 smaller sequences.

D. Vector Construction

Two different vectors were constructed: CaMVantiT1V1 end E8antiT1V1.

1. CaMVantiT1V1

The first vector, CaMVantiT1V1, contains the cauliflower mosaic virus 35S promoter and acid invertase antisense DNA. The cauliflower mosaic virus 35S is a constitutive promoter. Bases 1–1653 of the full length cDNA were ligated in the antisense orientation after the CaMV35S promoter in place of the GUS gene in pBI121 (Clontech Inc., La Jolla, Calif.). The plasmid was put into the Agrobacterium strain LBA 4404.

2. E8antiT1Z1

The second vector, E8antiT1V1, contains the prompter from the tomato E8 gene and acid invertase antisense DNA. The promoter from the tomato E8 gone is inducible in ripening tomato fruit. Bases 1–1653 of the full length cDNA were ligated in the antisense orientation between the E8 promoter region and the nos terminator region. This cassette was then ligated into pBIN19 (Clontech). The plasmid was put into the Agrobacterium strain LBA 4404.

E. Transformation of Tomato with Antisense Acid Invertase Constructions

Summary of the Procedure

The procedure followed was generally that of McCormick, *Plant Cell Reports*, 5:81–84 (1986). In brief, sterile cotyledon pieces were infected with Agrobacterium containing the plasmid 35SCaMV and/or the plasmid E8 containing the cDNA. The infected cotyledons were placed on feeder plates; this is the co-cultivation period. The cotyledons were then moved to plates containing selection/control antibiotics and zeatin. As callus forms and plantlets regenerate, they are moved to plates containing the same antibiotics, but no hormone. Plants that root are transferred to larger culture vessels without antibiotics or hormone and progagated or transplanted to soil.

1. Seed Sterilization

Seeds were sterilized in a solution of 50% commercial bleach and a few drops of wetting agent were added. After about 30–60 minutes, they were thouroughly rinsed in sterile water. Using sterile technique, they were transferred to germination plates.

2. Feeder Plate Preparation

The feeder plates are MSZ plates with a layer of tobacco feeder cells. About 3–4 ml of tobacco suspension cells were pipetted onto the feeder plates and spread evenly. A sterile Whatman #2 filter disk was placed on top of the cell layer.

3. Putting Cotyledons on the Feeder Plates

Sterile cotyledons are cut with a sterile #10 scalpel and transferred to the feeder plates. About 30–40 are put on each plate.

4. Infection with Transformed Agrobacterium

The cotyledons are transferred from the feeder plates to sterile petri dishes. Agrobacterium culture grown in Luria broth (LB) are poured over the cotyledons. After about 10 minutes, the cotyledons are removed to sterile filter paper, blotted dry, and transferred to feeded plates. They are incubated for 2–3 days.

5. Selection and Regeneration

The cotyledons are transferred to MSZ plates containing both control and selection antibiotics. As agroblooms occur, the cotyledons are transferred to fresh plates. As callus forms, the cotyledons are cut off and discarded. Shoots that arise from the callus are excised and transferred to MSB plates. Plants that root are transferred to a larger vessel.

6. Media, Reagents and Supplies

Media: Murshige and Skoog's salts
sucrose at 3%
inositol at 100%
Nitsch's vitamins
pH 5.8
agar noble at 0.8%
(This is the basic media or "MSB")
Make a 1000× sol. of the Nitsch's vits. Contents:

| | |
|---|---|
| thiamine HCl at 0.5 mg/l | 50 mg |
| nicotinic acid at 5.0 mg/l | 500 mg |
| glycine at 2.5 mg/l | 250 mg |
| pyridoxine at 0.5 mg/l | 50 mg |
| folic acid at 0.5 mg/l | 50 mg |
| d-biotin at .05 mg/l | 5 mg |

(store at −20° C., add to media before autoclaving)

Hormone:

Zeatin riboside trans-isomer; make a 1 mg/ml stock, titrate into solution with HCl, filter sterilize and store at −20° C.

Antibiotics:
Bacterial control:

| | |
|---|---|
| Carbenicillin | 300 mg/ml |
| Vancomycin | 100 mg/ml |
| Cefotaxime | 100 mg/ml |

Selection:

| | |
|---|---|
| Kanamycin | 50 mg/ml |

Antibiotics should be filter sterilized and stored at −20° C.

Plate Preparation:

Germination plates: MSZ with no hormone or antibiotics, pH 5.8, 0.8% agar.

MSZ plates: MSB with 2.0 mg/l Zeatin and antibiotics, pH 5.8, 0.8% agar.

MSB (rooting): Use 200 mg/l carbenicillin, 25 mg/l kanamycin.

7. Testing the Transformed Tomatos

The transformed tomato plants can be tested both for the expression of the antisense construct and the presence of the normal sense mRNA. First the RNA is isolated from the tissue desired with any appropriate RNA isolation procedure. A standard Northern blot is prepared, and probed with a radiolabelled DNA. To test for expression of the antisense construct, the DNA probe is made from the sense strand of the cloned gene. To test for the presense of the native RNA, the antisense strand of the cloned gene is labelled.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2223 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 20..1927

( x i ) SEQUENCE DESCRIPTION: SEQ ID NO:1:

```
GATTCCTCTA TCTTCTATT ATG GCC ACT CAG TGT TAT GAC CCC GAA AAC TCC    52
                     Met Ala Thr Gln Cys Tyr Asp Pro Glu Asn Ser
                      1               5                      10

GCC TCT CGT TAC ACA TTA CTC CCG GAT CAA CCC GAT TCC GGC CAC CGG    100
Ala Ser Arg Tyr Thr Leu Leu Pro Asp Gln Pro Asp Ser Gly His Arg
             15                  20                  25

AAG TCC CTT AAA ATC ATC TCC GGC ATT TTC CTC TCC GTT TTC CTT TTG    148
Lys Ser Leu Lys Ile Ile Ser Gly Ile Phe Leu Ser Val Phe Leu Leu
         30                  35                  40
```

| | | | | | | | | | | | | | | | | |
|---|---|---|---|---|---|---|---|---|---|---|---|---|---|---|---|---|
| CTT | TCT | GTA | GCC | TTC | TTT | CCG | ATC | CTC | AAC | AAC | CAG | TCA | CCG | GAC | TTG | 196 |
| Leu | Ser | Val | Ala | Phe | Phe | Pro | Ile | Leu | Asn | Asn | Gln | Ser | Pro | Asp | Leu | |
| | 45 | | | | 50 | | | | | 55 | | | | | | |
| CAA | ATC | GAC | TCC | CGT | TCG | CCG | GCG | CCG | CCG | TCA | AGA | GGT | GTT | TCT | CAG | 244 |
| Gln | Ile | Asp | Ser | Arg | Ser | Pro | Ala | Pro | Pro | Ser | Arg | Gly | Val | Ser | Gln | |
| 60 | | | | | 65 | | | | | 70 | | | | | 75 | |
| GGA | GTC | TCC | GAT | AAA | ACT | TTT | CGA | GAT | GTA | GCC | GGT | GCT | AGT | CAC | GTT | 292 |
| Gly | Val | Ser | Asp | Lys | Thr | Phe | Arg | Asp | Val | Ala | Gly | Ala | Ser | His | Val | |
| | | | | 80 | | | | | 85 | | | | | 90 | | |
| TCT | TAT | GCG | TGG | TCC | AAT | GCT | ATG | CTT | AGC | TGG | CAA | AGA | ACG | GCT | TAC | 340 |
| Ser | Tyr | Ala | Trp | Ser | Asn | Ala | Met | Leu | Ser | Trp | Gln | Arg | Thr | Ala | Tyr | |
| | | | 95 | | | | | 100 | | | | | 105 | | | |
| CAT | TTT | CAA | CCT | CAA | AAA | AAT | TGG | ATG | AAC | GAT | CCT | AAT | GGA | CCA | TTG | 388 |
| His | Phe | Gln | Pro | Gln | Lys | Asn | Trp | Met | Asn | Asp | Pro | Asn | Gly | Pro | Leu | |
| | | 110 | | | | | 115 | | | | | 120 | | | | |
| TAT | CAC | AAG | GGA | TGG | TAC | CAC | CTT | TTT | TAT | CAA | TAC | AAT | CCA | GAT | TCA | 436 |
| Tyr | His | Lys | Gly | Trp | Tyr | His | Leu | Phe | Tyr | Gln | Tyr | Asn | Pro | Asp | Ser | |
| | 125 | | | | | 130 | | | | | 135 | | | | | |
| GCT | ATT | TGG | GGA | AAT | ATC | ACA | TGG | GGC | CAT | GCT | GTA | TCC | AAG | GAC | TTG | 484 |
| Ala | Ile | Trp | Gly | Asn | Ile | Thr | Trp | Gly | His | Ala | Val | Ser | Lys | Asp | Leu | |
| 140 | | | | | 145 | | | | | 150 | | | | | 155 | |
| ATC | CAC | TGG | CTC | TAC | TTG | CCT | TTT | GCC | ATG | GTT | CCT | GAT | CAA | TGG | TAT | 532 |
| Ile | His | Trp | Leu | Tyr | Leu | Pro | Phe | Ala | Met | Val | Pro | Asp | Gln | Trp | Tyr | |
| | | | | 160 | | | | | 165 | | | | | 170 | | |
| GAT | ATT | AAC | GGT | GTC | TGG | ACA | GGG | TCC | GCT | ACC | ATC | CTA | CCC | GAT | GGT | 580 |
| Asp | Ile | Asn | Gly | Val | Trp | Thr | Gly | Ser | Ala | Thr | Ile | Leu | Pro | Asp | Gly | |
| | | | 175 | | | | | 180 | | | | | 185 | | | |
| CAG | ATC | ATG | ATG | CTT | TAT | ACC | GGT | GAC | ACT | GAT | GAT | TAT | GTG | CAA | GTG | 628 |
| Gln | Ile | Met | Met | Leu | Tyr | Thr | Gly | Asp | Thr | Asp | Asp | Tyr | Val | Gln | Val | |
| | | 190 | | | | | 195 | | | | | 200 | | | | |
| CAA | AAT | CTT | GCG | TAC | CCC | GCC | AAC | TTA | TCT | GAT | CCT | CTC | CTT | CTA | GAC | 676 |
| Gln | Asn | Leu | Ala | Tyr | Pro | Ala | Asn | Leu | Ser | Asp | Pro | Leu | Leu | Leu | Asp | |
| | 205 | | | | | 210 | | | | | 215 | | | | | |
| TGG | GTC | AAG | TTC | AAA | GGC | AAC | CCG | GTT | CTG | GTT | CCT | CCA | CCC | GGC | ATT | 724 |
| Trp | Val | Lys | Phe | Lys | Gly | Asn | Pro | Val | Leu | Val | Pro | Pro | Pro | Gly | Ile | |
| 220 | | | | | 225 | | | | | 230 | | | | | 235 | |
| GGT | GTC | AAG | GAC | TTT | AGA | GAC | CCG | ACT | ACT | GCT | TGG | ACC | GGA | CCA | CAA | 772 |
| Gly | Val | Lys | Asp | Phe | Arg | Asp | Pro | Thr | Thr | Ala | Trp | Thr | Gly | Pro | Gln | |
| | | | | 240 | | | | | 245 | | | | | 250 | | |
| AAT | GGG | CAA | TGG | CTG | TTA | ACA | ATC | GGG | TCT | AAG | ATT | GGT | AAA | ACG | GGT | 820 |
| Asn | Gly | Gln | Trp | Leu | Leu | Thr | Ile | Gly | Ser | Lys | Ile | Gly | Lys | Thr | Gly | |
| | | | 255 | | | | | 260 | | | | | 265 | | | |
| GTT | GCA | CTT | GTT | TAT | GAA | ACT | TCC | AAC | TTC | ACA | AGC | TTT | AAG | CTA | TTG | 868 |
| Val | Ala | Leu | Val | Tyr | Glu | Thr | Ser | Asn | Phe | Thr | Ser | Phe | Lys | Leu | Leu | |
| | | 270 | | | | | 275 | | | | | 280 | | | | |
| GAT | GGA | GTG | CTG | CAT | GCG | GTT | CCG | GGT | ACG | GGT | ATG | TGG | GAG | TGT | GTG | 916 |
| Asp | Gly | Val | Leu | His | Ala | Val | Pro | Gly | Thr | Gly | Met | Trp | Glu | Cys | Val | |
| | 285 | | | | | 290 | | | | | 295 | | | | | |
| GAC | TTT | TAC | CCG | GTA | TCT | ACT | AAA | AAA | ACA | AAC | GGG | TTG | GAC | ACA | TCA | 964 |
| Asp | Phe | Tyr | Pro | Val | Ser | Thr | Lys | Lys | Thr | Asn | Gly | Leu | Asp | Thr | Ser | |
| 300 | | | | | 305 | | | | | 310 | | | | | 315 | |
| TAT | AAC | GGG | CCG | GGT | GTA | AAG | CAT | GTG | TTA | AAA | GCA | AGT | TTA | GAT | GAC | 1012 |
| Tyr | Asn | Gly | Pro | Gly | Val | Lys | His | Val | Leu | Lys | Ala | Ser | Leu | Asp | Asp | |
| | | | | 320 | | | | | 325 | | | | | 330 | | |
| AAT | AAG | CAA | GAT | CAT | TAT | GCT | ATT | GGT | ACG | TAT | GAC | TTG | GGA | AAG | AAC | 1060 |
| Asn | Lys | Gln | Asp | His | Tyr | Ala | Ile | Gly | Thr | Tyr | Asp | Leu | Gly | Lys | Asn | |
| | | | | 335 | | | | | 340 | | | | | 345 | | |
| AAA | TGG | ACA | CCC | GAT | AAC | CCG | GAA | TTG | GAT | TGT | GGA | ATT | GGG | TTG | AGA | 1108 |
| Lys | Trp | Thr | Pro | Asp | Asn | Pro | Glu | Leu | Asp | Cys | Gly | Ile | Gly | Leu | Arg | |
| | | 350 | | | | | 355 | | | | | 360 | | | | |

| | | | | | | | | | | | | | | | |
|---|---|---|---|---|---|---|---|---|---|---|---|---|---|---|---|
| CTA | GAC | TAT | GGG | AAA | TAT | TAT | GCA | TCA | AAG | ACT | TTT | TAT | GAC | CCG | AAG | 1156
| Leu | Asp | Tyr | Gly | Lys | Tyr | Tyr | Ala | Ser | Lys | Thr | Phe | Tyr | Asp | Pro | Lys |
| 365 | | | | | 370 | | | | | 375 | | | | | |
| AAA | GAA | CGA | AGA | GTA | CTG | TGG | GGA | TGG | ATT | GGG | GAA | ACT | GAC | AGT | GAA | 1204
| Lys | Glu | Arg | Arg | Val | Leu | Trp | Gly | Trp | Ile | Gly | Glu | Thr | Asp | Ser | Glu |
| 380 | | | | | 385 | | | | | 390 | | | | | 395 |
| TCT | GCT | GAC | CTG | CAG | AAG | GGA | TGG | GCA | TCT | GTA | CAG | AGT | ATT | CCA | AGG | 1252
| Ser | Ala | Asp | Leu | Gln | Lys | Gly | Trp | Ala | Ser | Val | Gln | Ser | Ile | Pro | Arg |
| | | | | 400 | | | | 405 | | | | | 410 | | |
| ACA | GTG | CTT | TAC | GAC | AAG | AAG | ACA | GGG | ACA | CAT | CTA | CTT | CAG | TGG | CCA | 1300
| Thr | Val | Leu | Tyr | Asp | Lys | Lys | Thr | Gly | Thr | His | Leu | Leu | Gln | Trp | Pro |
| | | | 415 | | | | 420 | | | | | 425 | | | |
| GTG | GAA | GAA | ATT | GAA | AGC | TTA | AGA | GTG | GGT | GAT | CCT | ACT | GTT | AAG | CAA | 1348
| Val | Glu | Glu | Ile | Glu | Ser | Leu | Arg | Val | Gly | Asp | Pro | Thr | Val | Lys | Gln |
| | | 430 | | | | | 435 | | | | 440 | | | | |
| GTC | GAT | CTT | CAA | CCA | GGC | TCA | ATT | GAG | CTA | CTC | CGT | GTT | GAC | TCA | GCT | 1396
| Val | Asp | Leu | Gln | Pro | Gly | Ser | Ile | Glu | Leu | Leu | Arg | Val | Asp | Ser | Ala |
| | 445 | | | | | 450 | | | | | 455 | | | | |
| GCA | GAG | TTG | GAT | ATA | GAA | GCC | TCA | TTT | GAA | GTG | GAC | AAA | GTC | GCG | CTT | 1444
| Ala | Glu | Leu | Asp | Ile | Glu | Ala | Ser | Phe | Glu | Val | Asp | Lys | Val | Ala | Leu |
| 460 | | | | | 465 | | | | | 470 | | | | | 475 |
| CAG | GGA | ATA | ATT | GAA | GCA | GAT | CAT | GTA | GGT | TTC | AGT | TGC | TCT | ACT | AGT | 1492
| Gln | Gly | Ile | Ile | Glu | Ala | Asp | His | Val | Gly | Phe | Ser | Cys | Ser | Thr | Ser |
| | | | | 480 | | | | 485 | | | | | 490 | | |
| GGA | GGT | GCT | GCT | AGC | AGA | GGC | ATT | TTG | GGA | CCA | TTT | GGT | GTC | ATA | GTA | 1540
| Gly | Gly | Ala | Ala | Ser | Arg | Gly | Ile | Leu | Gly | Pro | Phe | Gly | Val | Ile | Val |
| | | | 495 | | | | 500 | | | | | 505 | | | |
| ATT | GCT | GAT | CAA | ACG | CTA | TCT | GAG | CTA | ACG | CCA | GTT | TAC | TTT | TAC | ATT | 1588
| Ile | Ala | Asp | Gln | Thr | Leu | Ser | Glu | Leu | Thr | Pro | Val | Tyr | Phe | Tyr | Ile |
| | | 510 | | | | | 515 | | | | 520 | | | | |
| TCT | AAA | GGA | GCT | GAT | GGT | CGT | GCA | GAG | ACT | CAC | TTC | TGT | GCT | GAT | CAA | 1636
| Ser | Lys | Gly | Ala | Asp | Gly | Arg | Ala | Glu | Thr | His | Phe | Cys | Ala | Asp | Gln |
| | 525 | | | | | 530 | | | | | 535 | | | | |
| ACT | AGA | TCC | TCT | GAG | GCT | CCG | GGA | GTT | GGT | AAA | CAA | GTT | TAT | GGT | AGT | 1684
| Thr | Arg | Ser | Ser | Glu | Ala | Pro | Gly | Val | Gly | Lys | Gln | Val | Tyr | Gly | Ser |
| 540 | | | | | 545 | | | | | 550 | | | | | 555 |
| TCA | GTA | CCT | GTG | TTG | GAC | GGT | GAA | AAA | CAT | TCA | ATG | AGA | TTA | TTG | GTG | 1732
| Ser | Val | Pro | Val | Leu | Asp | Gly | Glu | Lys | His | Ser | Met | Arg | Leu | Leu | Val |
| | | | | 560 | | | | | 565 | | | | | 570 | |
| GAT | CAC | TCA | ATT | GTG | GAG | AGC | TTT | GCT | CAA | GGA | GGA | AGA | ACA | GTC | ATA | 1780
| Asp | His | Ser | Ile | Val | Glu | Ser | Phe | Ala | Gln | Gly | Gly | Arg | Thr | Val | Ile |
| | | | 575 | | | | 580 | | | | | 585 | | | |
| ACA | TCG | CGA | ATT | TAC | CCA | ACA | AAG | GCA | GTA | AAT | GGA | GCA | GCA | CGA | CTC | 1828
| Thr | Ser | Arg | Ile | Tyr | Pro | Thr | Lys | Ala | Val | Asn | Gly | Ala | Ala | Arg | Leu |
| | | 590 | | | | | 595 | | | | | 600 | | | |
| TTT | GTT | TTC | AAC | AAT | GCC | ACA | GGG | GCT | AGC | GTT | ACT | GCC | TCC | GTC | AAG | 1876
| Phe | Val | Phe | Asn | Asn | Ala | Thr | Gly | Ala | Ser | Val | Thr | Ala | Ser | Val | Lys |
| | | 605 | | | | 610 | | | | | 615 | | | | |
| ATT | TGG | TCA | CTT | GAG | TCA | GCT | AAT | ATT | CAA | TCC | TTC | CCT | TTG | CAA | GAC | 1924
| Ile | Trp | Ser | Leu | Glu | Ser | Ala | Asn | Ile | Gln | Ser | Phe | Pro | Leu | Gln | Asp |
| 620 | | | | | 625 | | | | | 630 | | | | | 635 |

TTG TAATCTTCTT TATTTCGTTT TTTTTTTCTT TTTCATTTGA AGGTTATTTC    1977
Leu

ACCGACGTCC CATCAAGAAA GGGAAGAGGG AGATCAATAT ATGTAGTGTT ATTCGCCCTA    2037

CCTTAGGATT AGATGTCATC TAGCAATGTC AAATCTAGTA GAGTATACAA TGTATGGGTT    2097

CCTGGAAACC GAGTAGAGCT TACCTGGATT CTATGTAAAC TAAGAAAGCT CAGCAAATAT    2157

ATGCACAAAT AATTTACAGA AAAAAAAAAA AAAAAAAAAA AAAAAAAAAA AAAAAAAAA    2217

-continued ( 2 ) INFORMATION FOR SEQ ID NO:2:

( i ) SEQUENCE CHARACTERISTICS:
        ( A ) LENGTH: 636 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Thr Gln Cys Tyr Asp Pro Glu Asn Ser Ala Ser Arg Tyr Thr
 1               5                  10                  15
Leu Leu Pro Asp Gln Pro Asp Ser Gly His Arg Lys Ser Leu Lys Ile
            20                  25                  30
Ile Ser Gly Ile Phe Leu Ser Val Phe Leu Leu Leu Ser Val Ala Phe
        35                  40                  45
Phe Pro Ile Leu Asn Asn Gln Ser Pro Asp Leu Gln Ile Asp Ser Arg
    50                  55                  60
Ser Pro Ala Pro Pro Ser Arg Gly Val Ser Gln Gly Val Ser Asp Lys
65                  70                  75                  80
Thr Phe Arg Asp Val Ala Gly Ala Ser His Val Ser Tyr Ala Trp Ser
                85                  90                  95
Asn Ala Met Leu Ser Trp Gln Arg Thr Ala Tyr His Phe Gln Pro Gln
            100                 105                 110
Lys Asn Trp Met Asn Asp Pro Asn Gly Pro Leu Tyr His Lys Gly Trp
        115                 120                 125
Tyr His Leu Phe Tyr Gln Tyr Asn Pro Asp Ser Ala Ile Trp Gly Asn
    130                 135                 140
Ile Thr Trp Gly His Ala Val Ser Lys Asp Leu Ile His Trp Leu Tyr
145                 150                 155                 160
Leu Pro Phe Ala Met Val Pro Asp Gln Trp Tyr Asp Ile Asn Gly Val
                165                 170                 175
Trp Thr Gly Ser Ala Thr Ile Leu Pro Asp Gly Gln Ile Met Met Leu
            180                 185                 190
Tyr Thr Gly Asp Thr Asp Asp Tyr Val Gln Val Gln Asn Leu Ala Tyr
        195                 200                 205
Pro Ala Asn Leu Ser Asp Pro Leu Leu Leu Asp Trp Val Lys Phe Lys
    210                 215                 220
Gly Asn Pro Val Leu Val Pro Pro Gly Ile Gly Val Lys Asp Phe
225                 230                 235                 240
Arg Asp Pro Thr Thr Ala Trp Thr Gly Pro Gln Asn Gly Gln Trp Leu
                245                 250                 255
Leu Thr Ile Gly Ser Lys Ile Gly Lys Thr Gly Val Ala Leu Val Tyr
            260                 265                 270
Glu Thr Ser Asn Phe Thr Ser Phe Lys Leu Leu Asp Gly Val Leu His
        275                 280                 285
Ala Val Pro Gly Thr Gly Met Trp Glu Cys Val Asp Phe Tyr Pro Val
    290                 295                 300
Ser Thr Lys Lys Thr Asn Gly Leu Asp Thr Ser Tyr Asn Gly Pro Gly
305                 310                 315                 320
Val Lys His Val Leu Lys Ala Ser Leu Asp Asp Asn Lys Gln Asp His
                325                 330                 335
Tyr Ala Ile Gly Thr Tyr Asp Leu Gly Lys Asn Lys Trp Thr Pro Asp
            340                 345                 350
```

```
Asn Pro Glu Leu Asp Cys Gly Ile Gly Leu Arg Leu Asp Tyr Gly Lys
    355             360             365
Tyr Tyr Ala Ser Lys Thr Phe Tyr Asp Pro Lys Lys Glu Arg Arg Val
    370             375             380
Leu Trp Gly Trp Ile Gly Glu Thr Asp Ser Glu Ser Ala Asp Leu Gln
385             390             395                             400
Lys Gly Trp Ala Ser Val Gln Ser Ile Pro Arg Thr Val Leu Tyr Asp
                405             410             415
Lys Lys Thr Gly Thr His Leu Leu Gln Trp Pro Val Glu Glu Ile Glu
            420             425             430
Ser Leu Arg Val Gly Asp Pro Thr Val Lys Gln Val Asp Leu Gln Pro
        435             440             445
Gly Ser Ile Glu Leu Leu Arg Val Asp Ser Ala Ala Glu Leu Asp Ile
    450             455             460
Glu Ala Ser Phe Glu Val Asp Lys Val Ala Leu Gln Gly Ile Ile Glu
465             470             475                             480
Ala Asp His Val Gly Phe Ser Cys Ser Thr Ser Gly Gly Ala Ala Ser
                485             490             495
Arg Gly Ile Leu Gly Pro Phe Gly Val Ile Val Ile Ala Asp Gln Thr
            500             505             510
Leu Ser Glu Leu Thr Pro Val Tyr Phe Tyr Ile Ser Lys Gly Ala Asp
        515             520             525
Gly Arg Ala Glu Thr His Phe Cys Ala Asp Gln Thr Arg Ser Ser Glu
    530             535             540
Ala Pro Gly Val Gly Lys Gln Val Tyr Gly Ser Ser Val Pro Val Leu
545             550             555                             560
Asp Gly Glu Lys His Ser Met Arg Leu Leu Val Asp His Ser Ile Val
                565             570             575
Glu Ser Phe Ala Gln Gly Gly Arg Thr Val Ile Thr Ser Arg Ile Tyr
            580             585             590
Pro Thr Lys Ala Val Asn Gly Ala Ala Arg Leu Phe Val Phe Asn Asn
        595             600             605
Ala Thr Gly Ala Ser Val Thr Ala Ser Val Lys Ile Trp Ser Leu Glu
    610             615             620
Ser Ala Asn Ile Gln Ser Phe Pro Leu Gln Asp Leu
625             630             635
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( i x ) FEATURE:
        ( B ) LOCATION: 12
        ( D ) OTHER INFORMATION: fflabel= N is inosine ( i x ) FEATURE:
        ( B ) LOCATION: 15
        ( D ) OTHER INFORMATION: fflabel= N is inosine ( x i ) SEQUENCE DESCRIPTION: SEQ ID NO:3:

ATGGARTA YA CNGGNGA Y                         18

( 2 ) INFORMATION FOR SEQ ID NO:4:

```
    ( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: DNA (primer)

( i x ) FEATURE:
            ( B ) LOCATION: 4
            ( D ) OTHER INFORMATION: fflabel= N is inosine ( i x ) FEATURE:
            ( B ) LOCATION: 7
            ( D ) OTHER INFORMATION: fflabel= N is inosine ( i x ) FEATURE:
            ( B ) LOCATION: 16
            ( D ) OTHER INFORMATION: fflabel= N is inosine ( i x ) FEATURE:
            ( B ) LOCATION: 22
            ( D ) OTHER INFORMATION: fflabel= N is inosine ( x i ) SEQUENCE DESCRIPTION: SEQ ID NO:4:

RTANGCNARR  TT Y TCNAC Y T  GNACRTARTC                                    3 0
```

What is claimed is:

1. A method of increasing the sucrose content of fruit comprising, introducing into a tomato plant an expression cassette having a plant promoter sequence operably linked to a DNA subsequence of at least 20 base pairs derived from a DNA sequence encoding tomato acid invertase, the DNA subsequence being operably linked to the promoter sequence in an antisense orientation, and selecting resulting plants bearing fruit having increased soluble solids.

2. A method as in claim 1 wherein the promoter sequence is inducible.

3. A method as in claim 1 wherein the promoter is constitutive.

4. A method as in claim 1 wherein the expression cassette is introduced into the plant using Agrobacterium.

5. A method as in claim 1 wherein the expression cassette is introduced into the plant by a sexual cross.

6. A method of improving tomato fruit comprising:

introducing into a tomato plant an expression cassette having a promoter sequence operably linked to a nucleic acid sequence from a tomato invertase gene, wherein transcription of the nucleic acid sequence inhibits expression of an endogenous invertase gene; and selecting resulting plants bearing fruit having increased soluble solids.

7. The method of claim 6, wherein the nucleic acid sequence is SEQ. ID. No. 1.

8. The method of claim 6, wherein the nucleic acid sequence is operably linked to the promoter in an antisense orientation.

9. The method of claim 1 wherein the DNA sequence is SEQ. ID. No. 1.

* * * * *